US007919600B2

(12) United States Patent
Mills, Jr. et al.

(10) Patent No.: US 7,919,600 B2
(45) Date of Patent: Apr. 5, 2011

(54) COMPOSITIONS THAT REVERSIBLY GEL AND DE-GEL

(75) Inventors: Allen P. Mills, Jr., Riverside, CA (US); Bernard Yurke, Plainfield, NJ (US)

(73) Assignee: Alcatel-Lucent USA Inc., Murray Hill, NJ (US)

( * ) Notice: Subject to any disclaimer, the term of this patent is extended or adjusted under 35 U.S.C. 154(b) by 1495 days.

(21) Appl. No.: 10/252,287

(22) Filed: Sep. 23, 2002

(65) Prior Publication Data

US 2004/0059102 A1 Mar. 25, 2004

(51) Int. Cl.
*C07H 21/04* (2006.01)
*C12Q 1/68* (2006.01)
(52) U.S. Cl. ............................ 536/22.1; 536/23.1; 435/6
(58) Field of Classification Search ................. 536/23.1, 536/22.1; 514/44; 435/6; 530/300, 350
See application file for complete search history.

(56) References Cited

U.S. PATENT DOCUMENTS

| 5,175,270 | A | * | 12/1992 | Nilsen et al. ............... 536/24.32 |
| 5,736,316 | A | * | 4/1998 | Irvine et al. ...................... 435/5 |
| 5,770,358 | A | * | 6/1998 | Dower et al. ..................... 435/6 |
| 5,858,653 | A | * | 1/1999 | Duran et al. ..................... 435/6 |
| 6,083,726 | A |  | 7/2000 | Mills, Jr. et al. |
| 6,150,102 | A |  | 11/2000 | Mills, Jr. et al. |
| 6,214,187 | B1 |  | 4/2001 | Hammond et al. |
| 6,251,660 | B1 |  | 6/2001 | Muir et al. |
| 6,342,250 | B1 |  | 1/2002 | Masters |
| 6,368,356 | B1 |  | 4/2002 | Zhong et al. |
| 6,372,813 | B1 |  | 4/2002 | Johnson et al. |
| 6,391,937 | B1 |  | 5/2002 | Beuhler et al. |
| 6,410,044 | B1 |  | 6/2002 | Chudzik et al. |
| 6,537,747 | B1 | * | 3/2003 | Mills et al. .......................... 435/6 |
| 6,696,285 | B1 | * | 2/2004 | Mills et al. ................... 435/285.1 |
| 2003/0092838 | A1 | * | 5/2003 | Fomperie et al. ................ 525/71 |
| 2004/0062808 | A1 | * | 4/2004 | Langrana et al. ............. 424/486 |

FOREIGN PATENT DOCUMENTS

DE 19905793 A1 2/1999

OTHER PUBLICATIONS

Lewin B. DNA is the genetic material. Genes IV, 4th edition, p. 57-74, 1990.*
Rehman et al. Immobilization of acrylamide-modified oligonucleotides by co-polymerization. Nucleic Acids Res., vol. 27, No. 2, pp. 646-655, 1999.*
Simmel et al. Using a DNA construct and power a nanoactuator. Physical Review E, vol. 63, pp. 041913-1 0419131-5, 2001.*
"Acrydite Modified Custom Oligonucleotides—An Overview of Acrylamide Attachment Chemistry"; Apogent Discoveries Inc. 2001; pp. 1-4.
Phil Hammond, Lawrence Weir, Natalia Mamaeva, Mary Kenney, Satyagit Ray and Chris Boles; "Acrydite Gel Technology: Accelerated Hybridization Using Co-Polymerized DNA Probes"; Mosaic Technologies, Jan. 1998; pp. 1-14.
Farah N. Rehman, Mark Audeh, Ezra S. Abrams, Philip W. Hammond, Mary Kenney and T. Christian Boles; "Immobilization of Acrylamide-Modified Oligonucleotides by Co-Polymerization"; Nucleic Acids Research, 1999, vol. 27 No. 2; pp. 649-655.
"Biochemistry"; Fourth Edition by Lubert Stryer, W.H. Freeman and Company, New York 1995, pp. 75-90.
"Chemistry", Six Edition by Brown, Lemay and Burstein, Prentice Hall, Englewood Cliffs, New Jersey, 1994, pp. 378.
Simmel, Fredrich C., et al.; "Using DNA to construct and power a nanoactuator"; Physical Review E, vol. 63, 2001 The American Physical Society; pp. 041913-1-041913-5.
Lewin, Benjamin, "DNA is the Genetic Material"; Genes IV, 4th edition, 1990; pp. 57-74.
Rehman, Farah N., et al.; "Immobilization of acrylamide-modified oligonucleotides by co-polymerization"; Nucleic Acids Research, 1999, vol. 27, No. 2, pp. 649-655.
Hammond, Phil et al.; "Acrydite Gel Technology: Accelerated hybridization using co-polymerized DNA probes"; Mosaic Technologies, Jan. 1998; pp. 1-14.
"Acrydite Modified Custom Oligonucleotides—An Overview of Acrylamide Attachment Chemistry"; Apogent Discoveries; 2001; pp. 1-4.
Bischoff, Farideh Z., et al.; "Cell-free fetal DNA in maternal blood: kinetics, source and structure"; Human Reproduction Update; European Society of Human Reproduction and Embryology 2004; pp. 1-9.
Muller, Jurgen R., et al.; "Stimulation of Murine B Lymphocytes Induces a DNA Exonuclease Whose Activity on Switch-u DNA is Specifically Inhibited by Other Germ-Line Switch Region RNAs"; The American Association of Immunologists; The Journal of Immunology; 1998; pp. 3337-3341.
Rebowski, Grzegorz, et al.; "Antisense hairpin loop oligonucleotides as inhibitors of expression of multidrug resistance-associated protein 1: Their stability in fetal calf serum and human plasma"; Acta Biochimica Polonica—Reduction of MRP1 Expression; vol. 48 No. 4/2001; pp. 1061-1076.
Famulski, Konrad S., et al.; "Purification and characterization of a novel human acidic nuclease/intra-cyclobutylpyrimidine-dimer-DNA phosphodiesterase"; Biochem. J. (2000); pp. 583-593.
Kwon, Hyung-Joo, et al.; "Identification of an endonuclease secreted by human B lymphoblastic IM9 cells"; The International Journal of Biochemistry & Cell Biology 30 (1998); pp. 217-233.
Reynolds, Jason E., et al.; "Intracellular acidification is associated with, but not required for caspase activation, DNA fragmentation or apoptosis"; International Journal of Oncology 11 (1997); pp. 1241-1246.
Krieser, Ronald J., et al.; "Deoxyribonuclease II: structure and chromosomal localization of the murine gene, and comparison with the genomic structure of the human and three *C. elegans* homologs"; 2000 Elsevier Science, Gene 252 (2000); pp. 155-162.
Kirzon, SS, et al.; "Changes in the activity of endonucleosis of nuclear-dna in children with acute-leukemia" Gematologiya and Transfuziologiya, 40 (3): May 8-10-Jun. 1995 (Abstract); 1 Page.
Kim, Kwon HJ.; "Properties of the endonuclease secreted by human B lymphoblastic IM9 cells"; Journal of Biochemistry and Molecular Biology 31 (1): 106-110 Jan. 31, 1998; 1 Page.
Uhlmann, Eugen, et al.; "Studies on the Mechanism of Stabilization of Partially Phosphorothioated Oligonucleotides Against Nucleolytic Degradation"; Antisense & Nucleic Acid Drug Development 7; 1997; pp. 345-350.

* cited by examiner

*Primary Examiner* — Suryaprabha Chundrun
(74) *Attorney, Agent, or Firm* — Hitt Gaines, PC

(57) ABSTRACT

A composition that comprises a first polymer having first functional groups attached as side-chains thereto. The composition further comprises a second polymer having second functional groups attached as side-chains thereto. The first and the second functional groups are capable of reversibly forming a cross-link between the first and the second polymers.

8 Claims, 9 Drawing Sheets

SEQUENCE LISTING

<160> NUMBER OF SEQ ID NOS: 8

<210> SEQ ID NO 1
<211> LENGTH: 32
<212> TYPE: DNA
<213> ORGANISM: Artificial Sequence
<220> FEATURE:
<223> OTHER INFORMATION: Description of Artificial Sequence: a
      phosphoramidite modified oligonucleotide that serves as a
      cross-linking agent for a polya crylamide gel

<400> SEQUENCE: 1
agtacggaca ctagctggat ctgaggatta gt                                32

<210> SEQ ID NO 2
<211> LENGTH: 32
<212> TYPE: DNA
<213> ORGANISM: Artificial Sequence
<220> FEATURE:
<223> OTHER INFORMATION: Description of Artificial Sequence: a
      phosphoramidite modified oligonucleotide that serves as a
      cross-linking agent for a polyacry lamide gel

<400> SEQUENCE: 2
attcataccc ttagtatcgc acacacctac tt                                32

<210> SEQ ID NO 3
<211> LENGTH: 50
<212> TYPE: DNA
<213> ORGANISM: Artificial Sequence
<220> FEATURE:
<223> OTHER INFORMATION: Description of Artificial Sequence:
      a oligonucleotide that serves as a cross-linking agent
      for a polyacrylamide gel

<400> SEQUENCE: 3
actaatcctc agatccagct aagtaggtgt gtgcgatact ttacattgat             50

<210> SEQ ID NO 4
<211> LENGTH: 50
<212> TYPE: DNA
<213> ORGANISM: Artificial Sequence
<220> FEATURE:
<223> OTHER INFORMATION: Description of Artificial Sequence:
      a oligonucleotide that serves as a removal agent for a
      cross-linked polyacrylamide gel

<400> SEQUENCE: 4
atcaatgtaa agtatcgcac acacctactt agctggatct gaggattagt             50

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence:
      a phosphoramidite modified oligonucleotide that serves as
      a cross-linking agent for a polyacrylamide gel

<400> SEQUENCE: 5
tatgcacact gagtctgacg                                              20

<210> SEQ ID NO 6
<211> LENGTH: 20
<212> TYPE: DNA
<213> ORGANISM: Artificial Sequence
<220> FEATURE:

-continued

```
<223> OTHER INFORMATION: Description of Artificial Sequence:
      a phosphoramidite modified oligonucleotide that serves as
      a cross-linking agent for a polyacrylamide gel

<400> SEQUENCE: 6
atagcgagcg tcacgtatct                                                   20

<210> SEQ ID NO 7
<211> LENGTH: 40
<212> TYPE: DNA
<213> ORGANISM: Artificial Sequence
<220> FEATURE:
<223> OTHER INFORMATION: Description of Artificial Sequence:
      a oligonucleotide that serves as a cross-linking agent for
      a polyacrylamide gel

<400> SEQUENCE: 7
cgtcagactc agtgtgcata agatacgtga cgctcgctat                             40

<210> SEQ ID NO 8
<211> LENGTH: 40
<212> TYPE: DNA
<213> ORGANISM: Artificial
<220> FEATURE:
<223> OTHER INFORMATION: Description of Artificial Sequence:
      a oligonucleotide that serves as a removal agent for a
      cross-linked polyacrylamide gel

<400> SEQUENCE: 8
atagcgagcg tcacgtatct tatgcacact gagtctgacg                             40
```

COMPOSITIONS THAT REVERSIBLY GEL AND DE-GEL

CROSS-REFERENCE TO RELATED APPLICATION

This application is related to the disclosure of U.S. application Ser. No. 10/260,243, entitled "AN AGENT DELIVERY SYSTEM CAPABLE OF SELECTIVELY RELEASING AN AGENT", by Nosiher Langrana, David Lin and Bernard Yurke, filed on Sep. 30, 2002, commonly assigned with the present invention, and incorporated by reference as if reproduced herein in its entirety.

TECHNICAL FIELD OF THE INVENTION

The present invention is directed, in general, to a gel composition formed by cross-linking polymers.

BACKGROUND OF THE INVENTION

Polymers are used extensively in a wide range of medical applications such as biomaterials incorporated into drug delivery systems, diagnostic applications or prosthetic devices. The successful application of polymers for such purposes remains problematic, however. These problems reside in part due to the manner in which such polymers are cross-linked to form biomaterials.

For example, the use of polymers as gel compositions to encapsulate a drug requires that the structure of the gel composition produced from the polymers be carefully formulated to ensure the release of the drug over a desired interval of time. It may be difficult, however, using conventional gels to achieve the desired rate of release. In addition, the steps used to prepare the gel composition may be incompatible with the drug the gel composition is designed to contain. For example, the preparation of a polyacrylamide based cross-linked hydrogel typically involves the formation of a free radical on the growing polymer chain and cross-linking chains. Such free radicals or other chemical intermediaries may alter or inactivate the drug. Therefore, additional processing steps must be taken to prepare a capsule, and then add the drug to the capsule, often with the addition of waxes, fats or other filler material to help the capsule maintain its shape.

The use of polymers to make biomaterials comprising gel compositions used as prosthetic devices may be limited by the mechanical properties of the gel, or the synthetic procedures used to form such gels. It may be difficult, for example, to prepare a gel composition whose stress-strain relationship adequately mimics the biological material the gel is intended to replace, including soft tissues such as the nucleus pulposus present in intervertebral discs. Similar to that discussed above, the steps used to prepare the gel composition, resulting in the generation of free radicals for example, may make it undesirable to form the biomaterial in situ. Moreover, the monomer and cross-linking molecule may have toxicity or carcinogenic properties, such as acrylamide and N, N' methylene bis acrylamide. In certain applications, it may be desirable to alter the shape or mechanical properties of the biomaterial. For many conventional gel compositions this may necessitate the undesirable heating of the material.

Accordingly, what is needed in the art is a new gel composition that does not experience the problems associated with previous gels.

SUMMARY OF THE INVENTION

To address the above-discussed deficiencies, one embodiment of the present invention provides a gel composition comprising a first polymer and a second polymer. The first polymer has first functional groups attached as side-chains thereto. The second polymer has second first functional groups attached as side-chains thereto. The first and second functional groups are capable of reversibly forming a cross-link between the first and the second polymers.

In another embodiment, the invention provides a method for making a composition. The method includes preparing a first polymer having first functional groups attached as side-chains thereto. The method further includes preparing a second polymer having second functional groups attached as side-chains thereto. The method also comprises mixing the first and second polymers under conditions that cause the first functional groups to reversibly crosslink to the second functional groups.

Yet another embodiment is a second method for making a composition. The method comprises preparing a first and a second polymer having first and second functional groups attached as side-chains thereto, respectively. The method further includes mixing the first and second polymers. The method also includes adding a substance under conditions that cause the first and second functional groups to reversibly cross-link to the substance.

BRIEF DESCRIPTION OF THE DRAWINGS

The invention is best understood from the following detailed description, when read with the accompanying FIGUREs. Various features may not be drawn to scale and may be arbitrarily increased or reduced for clarity of discussion. Reference is now made to the following descriptions taken in conjunction with the accompanying drawings, in which.

DETAILED DESCRIPTION

One embodiment of the present invention is directed to a composition comprising a first and second polymer having first and second functional groups attached as side-chains thereto, respectively. The first and second functional groups are capable of reversibly forming a cross-link between the first and second polymers. The composition can change thereby from a viscous fluid state to a solid gel state as interactions between the functional groups cause more cross-linking between the polymers. The gel state may be achieved without changes in temperature (e.g., no cooling of the gel is required) and without the generation of undesirable free radicals or other intermediary chemicals. Moreover, the gel may be transformed back to the liquid state without heating the gel. Such gel compositions may be advantageously used as biomaterials for the delivery of agents to organisms or as a prosthetic device, and in electronic or optoelectronic devices.

Preferably, the cross-link is formed by a plurality of hydrogen bonds between the first and second functional groups. In certain embodiments, the addition of a substance causes the first and second functional groups to reversibly bind. Certain preferred embodiments of the present invention recognize the advantageous use of functional groups comprising nucleic acid sequences, attached as side-chains to polymers, to produce compositions.

Figure 1:
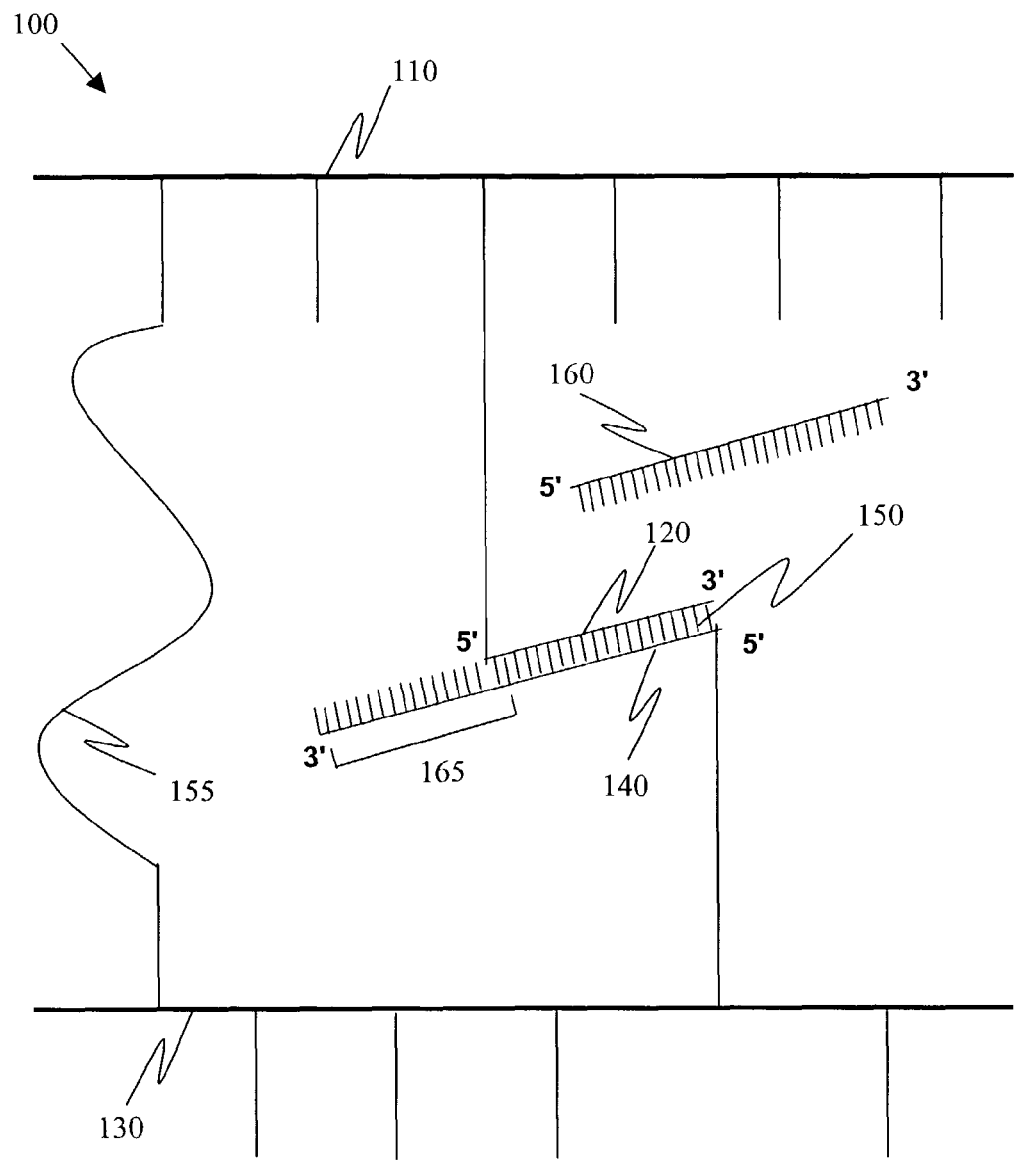
FIG. 1 schematically illustrates the cross-linking of two nucleic acid sequence-modified polymers comprising a composition formed by complementary base pairing of the sequences together according to the present invention.

FIG. 1 illustrates a schematic representation of a portion of one such composition 100. The gel composition 100 comprises a first polymer 110 having a first functional group comprising a nucleic acid sequence 120 attached as a side-chain thereto. The composition 100 further comprises a second polymer 130 having a second functional group comprising a nucleic acid sequence 140 attached as a side-chain thereto. The first and said second nucleic acid sequences 120, 140 are capable of reversibly forming a cross-link 150 between the first and second polymers 110, 130. The first and second polymers 110, 130 may comprise any polymer to which the nucleic acid sequences 120, 140 can be attached as side-chains thereto. In some preferred embodiments, for example, the first and second polymers 110, 130 may comprise a polymethylmethacrylate. In other preferred embodiments the first and second polymers 110, 130 comprises a polyacrylamide. In still other preferred embodiments, the first and second polymers 110, 130 comprised a polyvinyl alcohol. Other combinations are possible, where the first and second polymers 110, 130 are different polymers, for example, where the first polymer 110 is polyacrylamide while the second polymer 130 is polymethylmethacrylate.

In preferred embodiments such as that illustrated in FIG. 1, the first and said second nucleic acid sequences 120, 140 are capable of hybridizing to form reversible cross-links 150 comprising hydrogen bonds between complementary base portions of the first and the second nucleic acid sequences 120, 140. The term hybridization as used herein refers to the annealing of single-stranded nucleic acid fragments to form a double-stranded structure. The formation of such hydrogen bonds to form nucleic acid duplex structures is well known to those of ordinary skill in the art, and therefore need not be further explained herein. Depending on the length and identity of the nucleic acid sequence and environmental conditions under which the hybridization is performed (such as pH, ionic strength and temperature), the amount of base mismatch may range from 0% ("high complementarity") to up to 99% ("low complementarity"), and more preferably less than about 50% mismatch.

The first and said second nucleic acid sequences 120, 140 may separately comprise any naturally occurring nucleotide oligomers, or synthetically modified analogs of the oligomers. In certain preferred embodiments, for example, the nucleic acid sequences 120, 140 are separately selected from the group consisting of deoxyribonucleic acid (DNA); ribonucleic acid (RNA); peptide nucleic acids (PNA) and phosphorothioate analogs of DNA. The bases associated with the nucleotides comprising the nucleic acid sequences 120, 140 may comprise any naturally occurring nitrogen containing bases, such as purines or pyrimidines, or synthetically modified analog of the bases. In certain preferred embodiments, for example, where the one or both of the nucleic acid sequences 120, 140 comprise deoxyribonucleic acid, the bases may comprise adenine (A), guanine (G), cytosine (C), and thymine (T). In other preferred embodiments, for example, where one or both the nucleic acid sequences 120, 140 comprises ribonucleic acid, the thymine (T) base may be replaced by uracil (U).

The cross-links 150 have an association rate and a dissociation rate that are functions of a length of the first nucleic acid sequence 120 and a length of the second nucleic acid sequence 140. The term length as used herein refers to the number of bases present in the nucleic sequence of interest. In general, the longer the sequence, the slower the association and dissociation rate. Those of ordinary skill in the art understand that the rate of association and disassociation of nucleic acid sequences depends on the length of the DNA strands, the base sequence, and the degree of complementarity.

In addition, the cross-links 150 have an association rate and a dissociation rate that are functions of a percentage of complementarity between the first nucleic acid sequence 120 and the second nucleic acid sequence 140. Preferably, a sequence of at least ten bases in the first nucleic acid sequence is complementary to at least a portion of bases in the second nucleic acid sequence. More preferably, the percentage of complementarity between the first nucleic acid sequence 120 and the portion of bases in the second nucleic acid sequence 140 is at least about 50% and even more preferably at least about 99% complementary.

Moreover, the first nucleic acid sequence 120 and said second nucleic acid sequences 140 preferably has a minimal percentage of internal complementarity. Minimizing internal complementarity helps to prevent the formation of hairpin structures within either sequence. Preferably, the internal complementarity is less than 30% and even more preferably less than about 10%.

To promote the formation of the cross-link 150 between the first polymer 110 and the second polymer 130, in certain embodiments, the first nucleic acid sequence 120 and the second nucleic acid sequence 140 each comprise between about 5 and about 100 nucleotide bases. More preferably, they comprise between about 20 and about 30 nucleotide bases in length.

More than one pair of complementary nucleic acid sequences 120, 140 may be attached as side-chains to the first and second polymer 110, 130 to facilitate crosslinking. For example the side-chains of the first polymer 110 may comprise at least two first nucleic acid sequences 120 having at least one difference in a base sequence between the two first nucleic acid sequences 120. Similarly, the side-chains of the second polymer 130 may comprise at least two second nucleic acid sequences 140 having at least one difference between the two second nucleic acid sequences 140. Furthermore, crosslinking may further include a combination of cross-links 150 between nucleic acid sequences 120, 140, as discussed above, and conventionally formed cross-links 155 achieved, for example, through the addition of N, N' methylene bis acrylamide during polymerization of the first and second polymers 110, 130. Such embodiments advantageously allow for further adjustment of the transition of the composition from liquid to solid, as well to adjust the chemical and mechanical properties of the composition.

The dissociation of the cross-links 150 between the first and second polymer 110, 130 may be facilitated with the addition of a third nucleic acid sequence 160. Alternatively, the third nucleic acid sequence 160 may deter or prevent the formation of the cross-link 150. In certain embodiments, the third nucleic acid sequence 160 has between about 2 and about 20 nucleotide bases. Preferably, the third nucleic acid sequence is within 6 base pairs in length, and more preferably the same length as at least one of the first or second nucleic acid sequence 120, 140.

At least one of the first nucleic acid sequence 120 or the second nucleic acid sequence 140 further comprise a toe-hold nucleic acid sequence 165. The toe-hold nucleic acid sequence 165 is sufficiently complementary to the third nucleic acid sequence 160 that the third nucleic acid sequence 160 facilitates a dissociation of the cross-link 150. The extent of complementarity between the third nucleic acid sequence 160 and toe-hold nucleic acid sequence 165 is at least about 50% and more preferably at least about 90%, and may be adjusted to control the rate or the effectiveness of the breaking of the crosslink.

The toe-hold nucleic acid sequence 165 provides a region to which third nucleic acid sequence 160 can initially bind. Once the third nucleic acid sequence 160 has hybridized with the toe-hold nucleic acid sequence 165, the third nucleic acid sequence 160 competitively binds to remaining portions of one or both of the first and second nucleic acid sequences 120, 140. This competition causes unbinding of the first and second nucleic acid sequences 120, 140 and dissociation of the cross-link 150. The toe hold sequence is preferably shorter than the third nucleic acid sequence 160.

Figure 2:
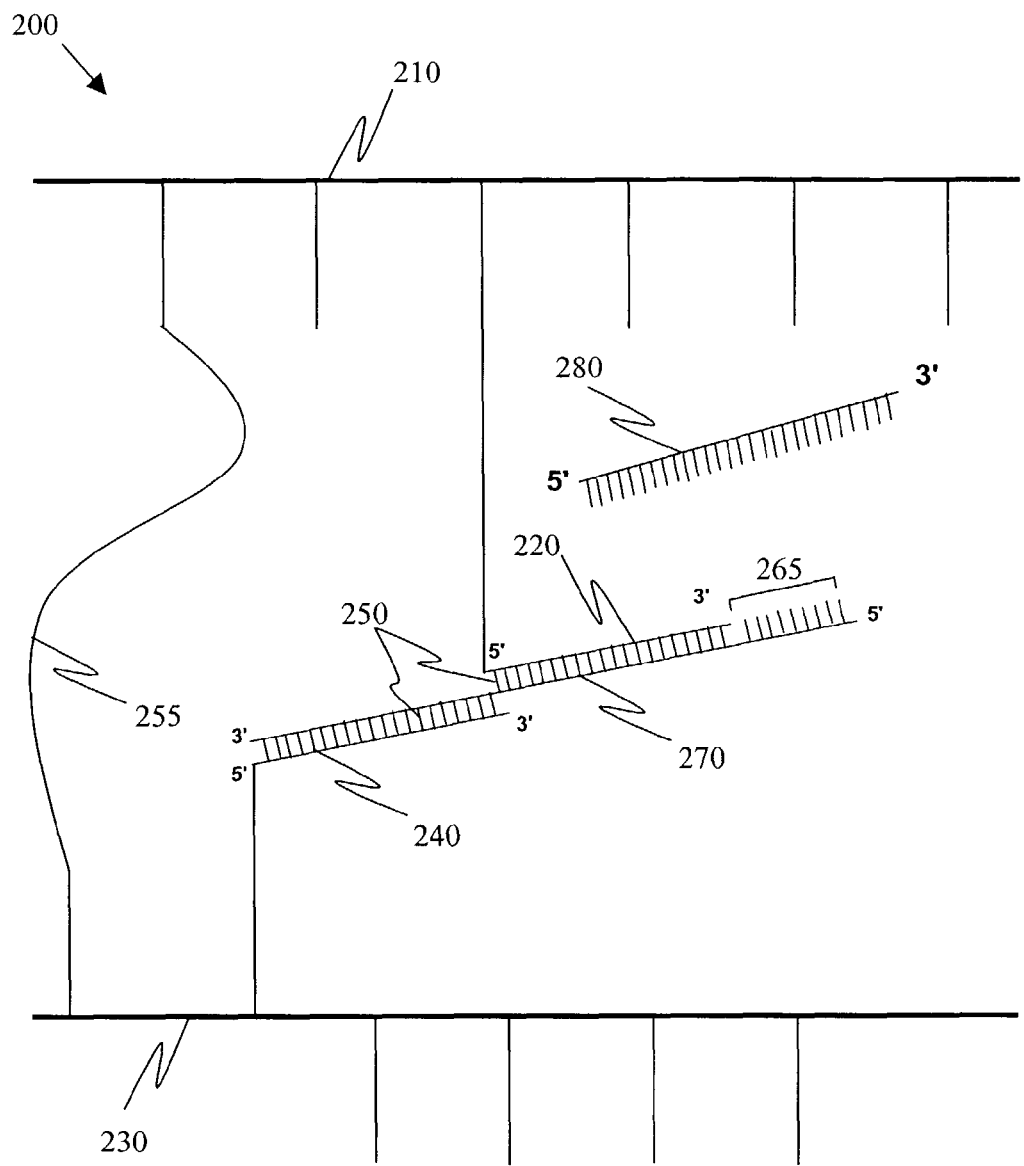
FIG. 2 schematically illustrates the cross-linking of two nucleic acid sequence-modified polymers comprising a composition formed by complementary base pairing of the sequences to a third nucleic acid sequence according to the present invention.

An alternative preferred embodiment of the gel composition 200, is illustrated in FIG. 2, wherein the reference numbers refer to like elements of the embodiment depicted in FIG. 1. Here, the gel composition 200 further includes a third nucleic acid sequence 270 that, when attached to the first and the second nucleic acid sequences 220, 240, facilitates formation of the cross-link 250. In this embodiment, therefore, the cross-link 250 includes the nucleotide backbone of the third nucleic acid sequence 270 and a plurality of hydrogen bonds between the third nucleic acid sequence 270 and the first and second nucleic acid sequence 220, 240. The third nucleic acid sequence 270 may be of any length sufficient to facilitate formation of the cross-link 250. In certain preferred embodiments, for example, the length of the third nucleic acid sequence 270 is at least as long as the combined length of the first and second nucleic acid sequences 220, 240.

Such alternative gel compositions 200 may further include a fourth nucleic acid sequence 280 that facilitates dissociation of the cross-links 250 between the first and second polymer 210, 230. Analogous to that discussed for the embodiment shown in FIG. 1, the third nucleic acid sequence 270 may further comprise a toe-hold nucleic acid sequence 265 that is sufficiently complementary to the fourth nucleic acid sequence 280 that the fourth nucleic acid sequence 280 facilitates a dissociation of the cross-link 250.

Certain preferred embodiments use the gel composition in a prosthetic device and electronic or optoelectronic devices. As further explained below, the prosthetic device may be capable of changing shape as a function of the extent of the cross-links 150 formed between first and the second polymers, 110, 130, via interactions between the first, second and third nucleic acid sequences 120, 140, 160 (FIG. 1), or via analogous interactions for the embodiment shown in FIG. 2. In certain embodiments, the prosthetic device may be capable of changing elastic modulus as a function of the extent of the above-mentioned cross-links. Non-limiting examples of the prosthetic device include: artificial spinal disk fluid; artificial ligaments; artificial bone; artificial valves; artificial skin; and dental prostheses.

Figure 3:
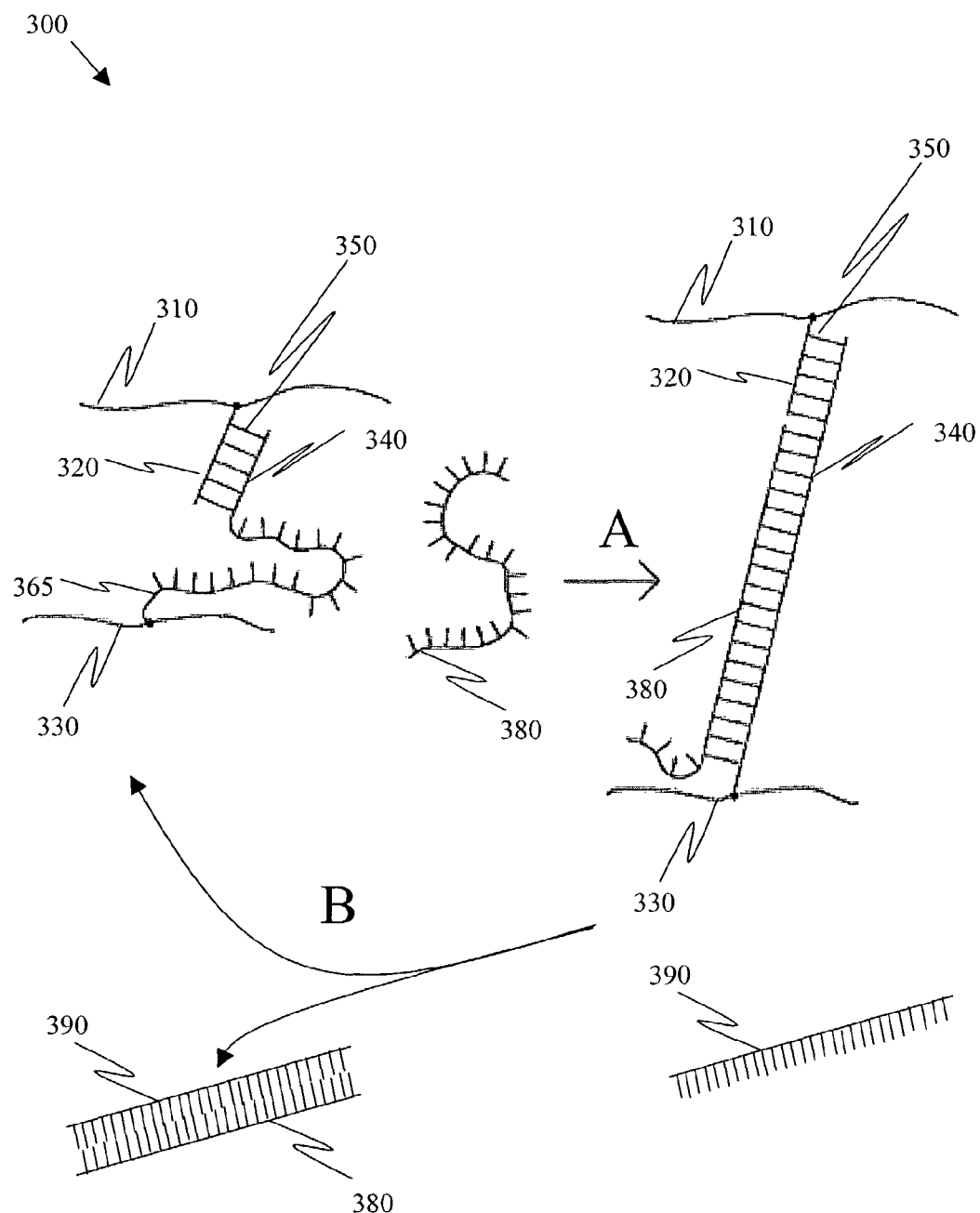
FIG. 3 schematically illustrates the swelling and shrinkage of a gel composition according to the present invention.

FIG. 3 illustrates one embodiment of how hybridization can cause the gel 300 to expand. The gel 300 has analogous structures and numbering scheme as discussed for FIG. 1. Such embodiments may further include a fourth nucleic acid sequence 380, preferably having about the same length and being complementary to the toe-hold nucleic acid sequence 365. The fourth nucleic acid sequence 380, rather than serving as a strand to break the crosslink, serve to straighten the toehold 365, so that the first polymer 310 and the second polymer 330, are pushed apart, thereby causing swelling of the composition 300 (arrow A).

Moreover, in such embodiments, the addition of a fifth nucleic acid sequence 390 that is complementary to the fourth nucleic acid sequence 380, could cause shrinkage of the composition 350 (arrow B). When the third and fourth nuclei acid sequences 390, 380 hybrid with each other, the first and second polymer 310, 330 would come closer together because of the conversion from a stiff double stranded section of the first or second nuclei acid sequence 320, 340, back to a more flexible single stranded section, thereby causing the composition 300 to shrink (arrow B).

Figure 4:
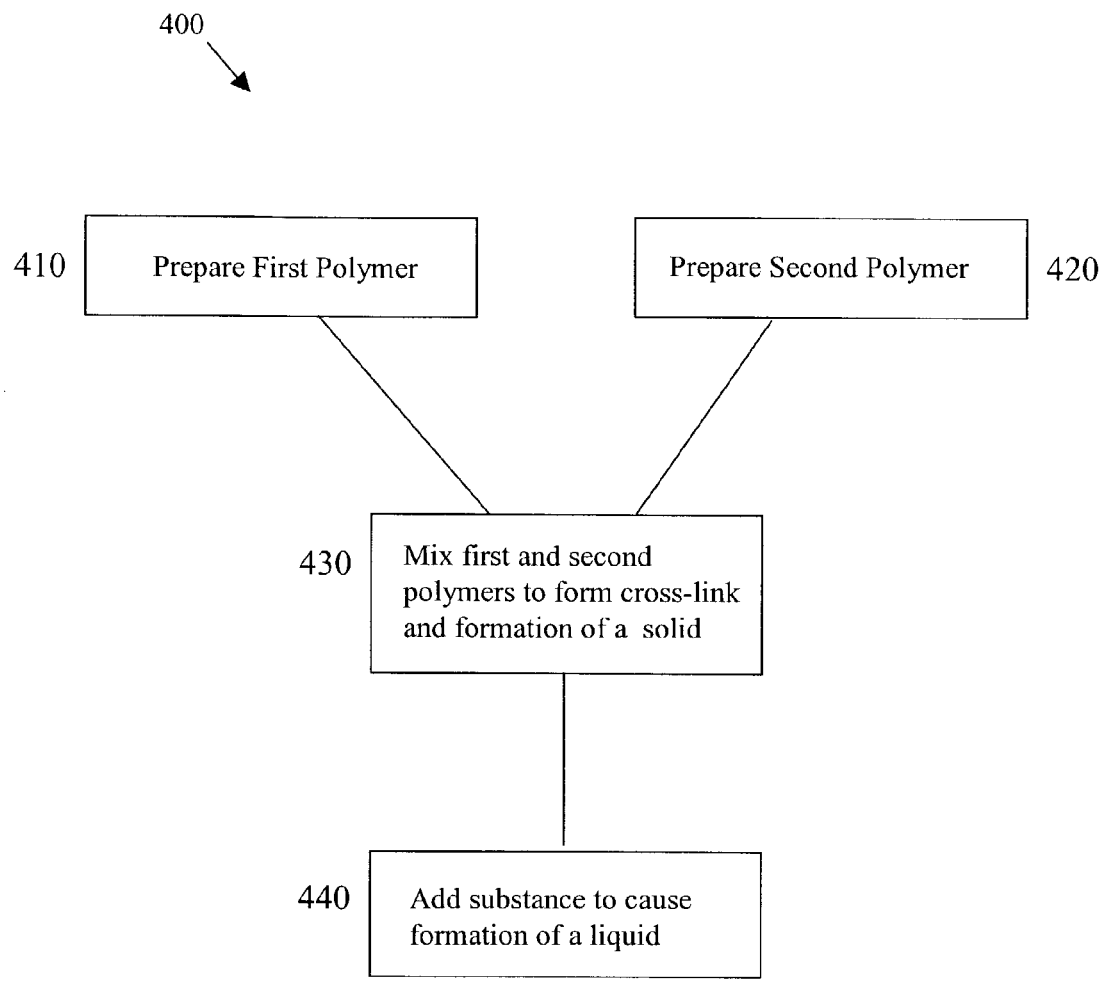
FIG. 4 illustrates, by flow diagram, a method for making a composition of the present invention.

Turning now to FIG. 4, illustrated is another embodiment of the present invention, a method 400 for making a composition. The method 400 comprises a step 410 of preparing a first polymer having first functional groups attached as side-chains thereto. In step 420, a second polymer having second functional groups attached as side-chains thereto is prepared. In step 430, the first and second polymers are mixed under conditions that cause the first functional groups to reversibly crosslink to the second functional groups. Preferably, the mixing causes the composition to change from a liquid to a solid.

Numerous methods, well known to those of ordinary skill in the art, may be used to prepare the first polymer and the second polymer in steps 410 and 420. Steps 410 and 420 may include modifying nucleic acid sequences with functional groups and attaching the functionalized nucleic acid sequences as side-chains to the first and second polymer or to monomeric units of the first and second polymer. In the latter such embodiments, preparation steps 410 and 420 then include separately mixing monomers of the first and second polymers with the functionalized first and the second nucleic acid sequences, respectively. The preparation steps 410, 420 may include adding a polymerization initiator and catalyst. The functional groups facilitate attachment of the modified first and second nucleic acid sequences as side-chains to the growing first and second polymers.

Exemplary functionalizations include: biotin-modified nucleic acid sequences non-covalently complexed with polymer comprising a protein, such as Streptavidin; thiol-modified nucleic acid sequences covalently linked via a disulfide bond to a polymer containing thiol groups; amine-modified nucleic acid sequences covalently linked to an activated carboxylate or an aldehyde group attached to a polymer; or the covalent attachment of nucleic acid sequences to polymers via acrylic linkages.

In certain preferred embodiments, the nucleic acid sequences are modified with a phosphoramidite having a general formula $CH_3-C(=CH_2)-CO-NH-(CH_2)_n-PO_4$, wherein n ranges from 1 to 18. One preferred phosphoramidite is $(CH_3-C(=CH_2)-CO-NH-(CH_2)_6-PO_4$. The phosphoramidite may be copolymerized with a monomer comprising acrylamide to form a polyacrylamide polymer having first and second nucleic acid sequences attached as side-chains thereto. When the monomer is acrylamide, the initiator preferably comprises ammonium persulfate and the catalyst preferably comprises tetramethylenediamine. Alternatively, the phosphoramidite-modified nucleic acid sequences can be reacted with a thiol to produce a thio-ether adduct that can then be bonded to monomers for subsequent use in polymerization.

The concentration of nucleic acids incorporated as side-chains into the polymer is determined by the ratio of moles of phosphoramidite modified nucleic acid sequences to moles of monomer. For example, the ratio of moles of the first and second nucleic acid sequence to moles of the acrylamide monomer, preferably ranges from about 1:1 to about 1:100.

As illustrated in FIG. 4, the method 400 may further include a step 440 of adding a substance that causes the first and second functional groups to unbind. Preferably the addition of the substance cause the solid gel to be converted to a liquid. In certain preferred embodiments, the substance is a third nucleic acid sequence, such as the third nucleic acid sequence 160 depicted in FIG. 1. In such embodiments, as noted elsewhere herein, preferably one or both of the first or second nucleic acid sequences further comprise a toe-hold nucleic sequence.

Figure 5:
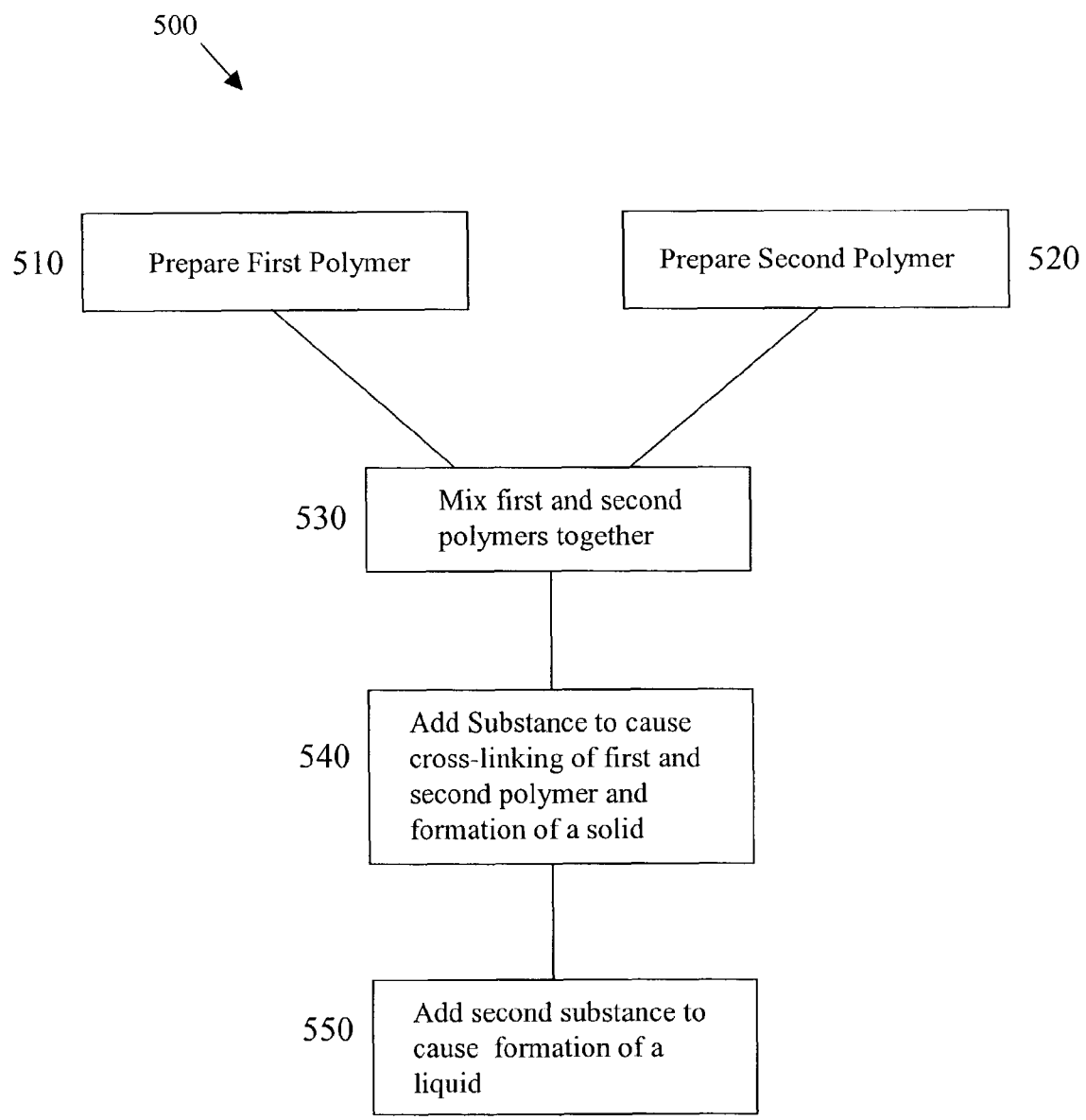
FIG. 5 illustrates, by flow diagram, a second method for making a composition of the present invention.

Another method 500 for making a composition according to the present invention is illustrated in FIG. 5. In step 510, a first polymer having first functional groups attached as side-chains thereto is prepared. In step 520, a second polymer having second functional groups attached as side-chains thereto is prepared. In step 530, the first and second polymers are mixed together. In step 540, a substance is added under conditions that cause the first and second functional groups to reversibly crosslink to the substance.

In one preferred embodiment of the method 500, the first and second functional groups are first and second single stranded nucleic acid sequences and the substance is a third nucleic acid sequence, such as the third nucleic acid sequence 270 depicted in FIG. 2. The third nucleic acid sequence is capable of attaching to the first and second nucleic acid sequences to facilitate formation of the cross-link. Certain embodiments may further include a step 550, of adding a second substance, for example, a fourth nucleic acid sequence, that facilitates a dissociation of the cross-link. Analogous to previously discussed embodiments, the third nucleic acid sequence further comprises a toe-hold nucleic acid sequence complementary to the fourth nucleic acid sequence.

Having described various embodiments, it is believed that the invention will become even more apparent by reference to the following examples. It will be appreciated that the examples are presented solely for the purpose of illustration and should not be construed as limiting the invention. For instance, although the experiments described below may be carried out in laboratory or pilot plant setting, one skilled in the art could adjust specific numbers, dimensions and quantities up to appropriate values for a full scale plant.

EXPERIMENTS

Experiments were conducted to examine: 1) the preparation of a polyacrylamide gel crossed linked via a nucleic acid sequence according to the present invention and the ability to prevent cross-linking with an oligomer comprising a nucleic acid sequence added to the gel; and 2) the different mechanical properties of the nucleic acid cross-linked gel.

Experiment 1

The nucleic acid sequences were DNA strands designated as SA1, SA2, L1, and R1, the specific sequences as defined below:

(SEQ ID NO.: 1)
SA1: 5' Phosphoramidite-AGTACGGACACTAGCTGGATCTGAGG ATTAGT (SEQ ID NO.: 2)
SA2: 5' Phosphoramidite-ATTCATACCCTTAGTATCGCACACAC CTACTT (SEQ ID NO.: 3)
L1: 5' ACTAATCCTCAGATCCAGCTAAGTAGGTGTGTGCGATACTTTA CATTGAT (SEQ ID NO.: 4)
R1: 5' ATCAATGTAAAGTATCGCACACACCTACTTAGCTGGATCTGAG GATTAGT Through their functionalization with a phosphoramidite (e.g., Product AC-350 from Apogent Discoveries, Hudson N.H.), SA1 and SA2 can be incorporated into polyacrylamide. The linking strand "L1" hybridizes with both SA1 and SA2 and serves to crosslink the gel. The removal strand "R1" is complementary to the L1 strand, and was used to test the ability to prevent the re-association of SA1, SA2 and L1, as further described below. All DNA strands were purchased in High Performance Liquid Chromatography or Polyacrylamide Gel Electrophoresis purified grades from Operon Technologies, Inc. (now QIAGEN Operon, Inc., Alameda, Calif.) or Integrated DNA Technologies (Coralville, Iowa).

SA1 and SA2 were separately polymerized with acrylamide. Separate stock solutions of SA1 and SA2 were prepared at a concentration of 1 mM in TE buffer (10 mM Tris, 1 mM EDTA, pH 8.0). A five mL solution comprising 40% acrylamide monomer in $H_2O$, 30 ml of SA1 stock solution, 10 ml of $H_2O$, and 5 ml of 10× TBE buffer (a 10 times concentrate of 89 mM Tris-borate, 2.5 mM EDTA, pH 8.3 at 20° C.) was mixed together. Dry nitrogen was bubbled through the mixture for 5 min. An initiator solution consisting of 0.5 ml $H_2O$, 0.05 g ammonium persulfate and 25 ml N,N,N',N'-Tetramethylethylenediamine (TEMED) was prepared shortly before use (less than about 6 hours). About 0.7 ml of this solution was added to the SA1 mixture. Nitrogen was bubbled through the mixture for another 20 minutes as polymerization took place and the fluid became viscous. An SA2 mixture was similarly prepared. The SA1 and SA2 solutions were then mixed together and water was added to account for evaporative loss by bringing the total volume of the fluid to 100 ml. To one 33 ml portion of this solution, designated as the cross-linked mixture, 10 ml of L1 stock solution was added. To another 33 ml portion of this solution, designated as the control solution, 10 ml of TE buffer was added.

A ~1 mm diameter sapphire sphere was used to measure the viscosity of the fluids by monitoring the rate at which the sapphire sphere moved through the fluid under the force of gravity for a period of time (from about 1.5 s to about 105 s) at progressively increasing temperatures ranging from about 20° C. to about 60° C. For example, at room temperature, in the control mixture, the sphere sank at a rate of ~0.1 cm/sec. In contrast, in the cross-linked mixture, no movement of the sphere was detectable, indicating that the velocity was less than about $3 \times 10^{-5}$ cm/sec.

The measured velocities for the sapphire sphere were converted into viscosities using Stokes law:

$$F = m \cdot g = \pi \cdot \eta \cdot r \cdot v \tag{1}$$

where m is the boyant mass of the sphere (gm), g the acceleration due to gravity (cm/s$^2$), $\eta$ the viscosity (Poise), r the diameter of the sphere (cm), and v is the velocity with which the sphere moves through the fluid (cm/s). Given that the density of sapphire is 3.965 g/cm$^3$, the viscosity in poise is given by:

$$\eta = 1.6 \cdot (g/s^2) \cdot (1/v) \quad (2)$$

Figure 6:
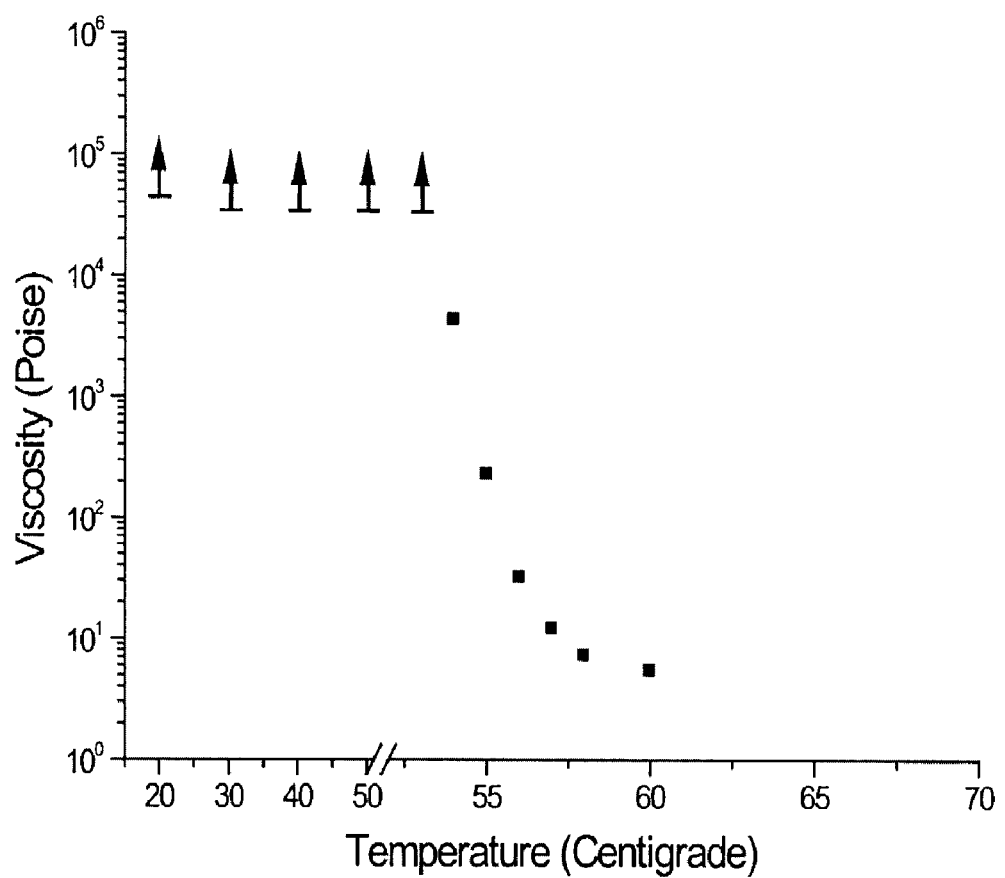
FIG. 6 illustrates the relationship between temperature and viscosity for a representative composition of the present invention.

As illustrated in FIG. 6, below about 54° C., the crosslinked mixture exhibited no detectable flow, and behaved like a gel. Hence, the bars with upward arrows in FIG. 6 indicate lower bounds. For comparison, the viscosity of water at −20° C. equals about 1×10$^{-2}$ Poise. When the cross-linked mixture was heated above the expected melting temperature of DNA (defined as the temperature at which half of the double strands are dissociated), the gel became fluid and the viscosity decreased.

After performing the melting study, the removal strand R1 was added to the cross-linked mixture at ~55° C. and the solution was mixed for about 8 minutes. The resulting solution was then cooled to ~20° C. and viscosity measurements were repeated, by monitoring the rate at which the sapphire sphere moved through the fluid, as described above. A viscosity of about 7 Poise was determined, as compared to the lower bound of viscosity of about 54,000 Poise measured in the original cross-linked mixture (see FIG. 5). This demonstrates that the R1 strand was capable of preventing cross-link formation.

Experiment 2

The viscosity of gel compositions of the present invention were examined at different degrees of cross-link density and as a function of temperature. In addition, the elastic modulus of certain gel compositions were measured.

Two DNA strands designated SA3 and SA4 comprised of random DNA sequences and 20 bases in length were functionalized at the 5' end with a phosphoramidite. Sections complementary to SA1 and SA2 were each incorporated into a cross-linker strand L2 of 50 bases. The additional 10 bases, designated as a toe-hold nucleic acid sequence, served as a point of attachment at which a removal strand R2 attaches to L2 thereby promoting dissociation of the cross-link. The specific sequences are as defined below:

```
                                      (SEQ ID NO.: 5)
SA3: 5' Phosphoramidite-TATGCACACTGAGTCTGACG (SEQ ID NO.: 6)
SA4: 5' Phosphoramidite-ATAGCGAGCGTCACGTATCT (SEQ ID NO.: 7)
L2:  5' CGTCAGACTCAGTGTGCATAAGATACGTGACGCTCGCTAT (SEQ ID NO.V 8)
R2:  5' ATAGCGAGCGTCACGTATcTTATGCACACTGAGTCTGACG
```

SA3 and SA4 were separately incorporated into polyacrylamide, similar to that described in Experiment 1, and then mixed to form 26 μL of a pre-gel mixture comprising: ~0.43 wt % SA3; ~0.42 wt % SA4; and ~3 wt % acrylamide in TBE buffer. A ~0.79 mm diameter sapphire bead was placed in the pre-gel mixture, the container holding the mixture and bead was sealed, and then the container was placed in a temperature-controlled water bath. Next, a series of viscosity measurements as a function of temperature from ~27 to ~85° C. were made, similar to that described in Experiment 1. The container was then removed from the bath, and a volume of L2 was added to the mixture to form a gel composition comprising ~0.06 wt % L2. This amount equals ~5.6% of the stoichiometric amount for complete hybridization to the SA3 and SA4 strands (i.e., ~5.6:100:100 of L2:SA3:SA4). Water was evaporated off from the mixture to provide substantially the same volume as the pre-gel mixture. The container was then resealed, returned to the water bath, and another series of viscosity measurements as a function of temperature were made. This process was repeated several times with step-wise additions of L2 to the gel composition, until a ~100:100:100 stoichiometry of L2:SA3:SA4 was attained (~1 wt % L2).

Figure 7:
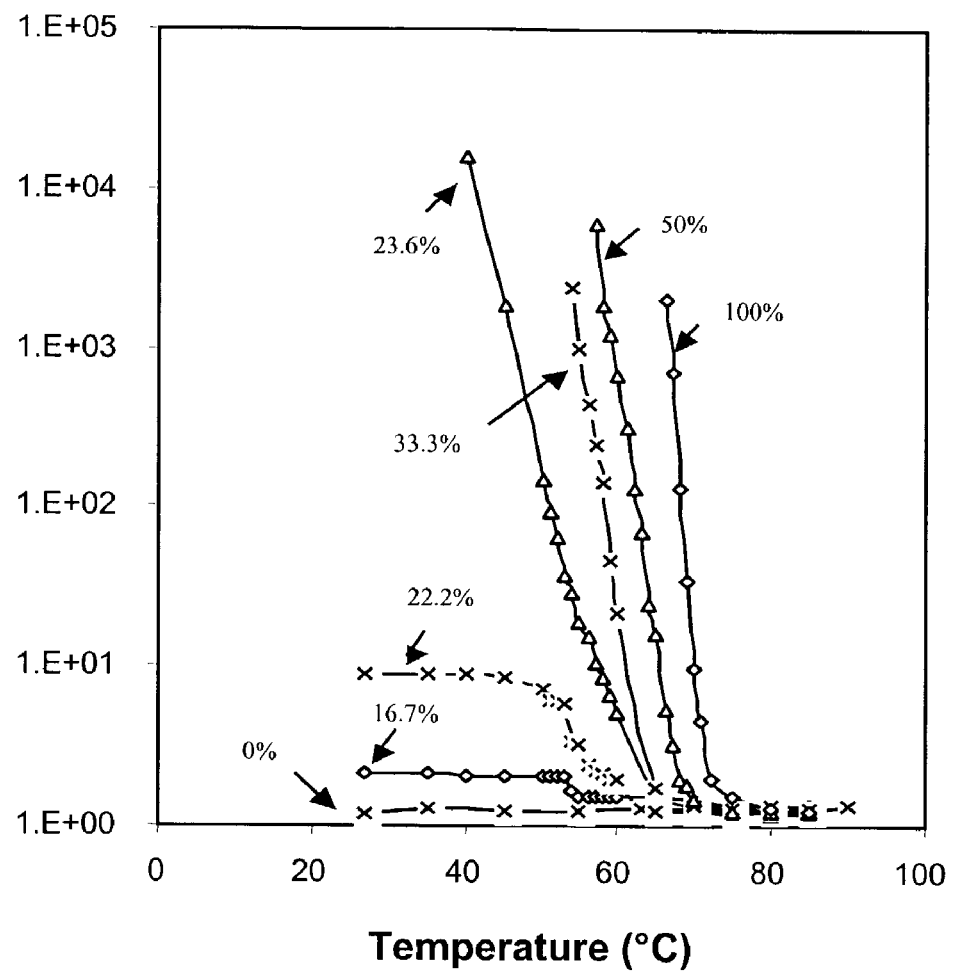
FIG. 7 illustrates the relationship between temperature and viscosity for representative compositions of the present invention having different amounts of a nucleic acid sequence serving as a cross-linker.

Selected results from these measurements are depicted in FIG. 7. The results in FIG. 7 illustrate that in the absence of cross-linker L2, the viscosity was substantially constant from ~27 to ~85° C. In contrast, as L2 was added, viscosity at ~27° C. increased as a nonlinear function of the amount of cross-linker L2 present. In particular, there was a large increase in the viscosity when the amount of L2 increased from ~22.2% to ~23.6% of the stoichiometric amount for complete hybridization. Thus, for this particular combination of SA3, SA4, and L2, a cross-linker concentration of at least about 23% of the stoichiometric amount of L2 is preferred to facilitate optimal gel formation. For gels containing ~23.6% of the stoichiometric amount of L2 and higher, the viscosity decreased in a nonlinear fashion with respect to increasing temperature.

Figure 8:
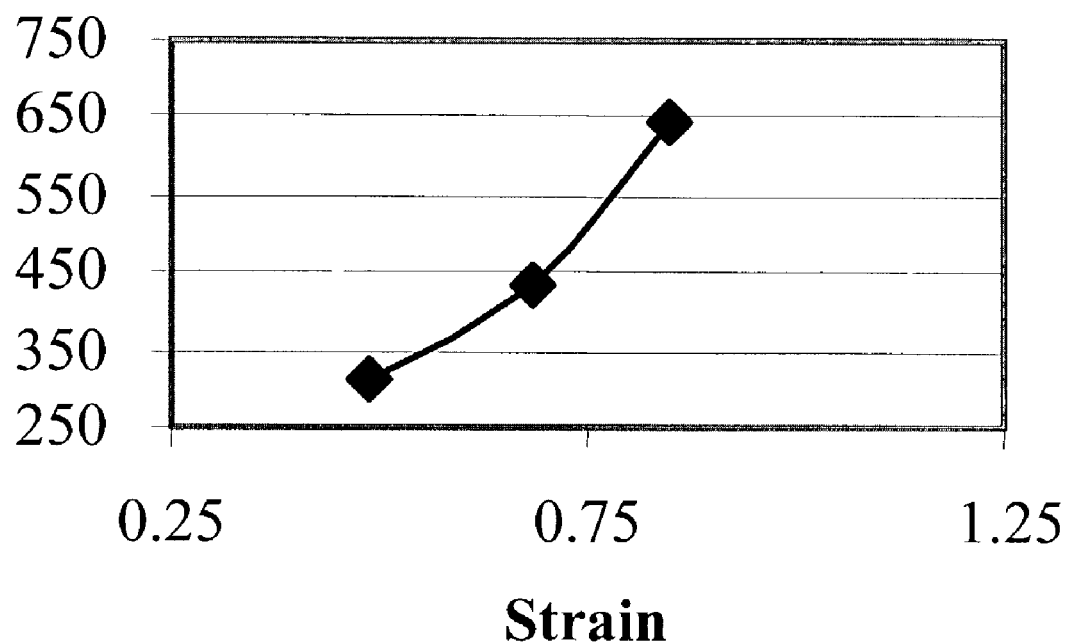
FIG. 8 illustrate the stress-strain relationship for a representative composition of the present invention.

Another series of experiments were conducted using these same DNA strands to measure the elastic modulus of particular gel compositions. For example, one such gel composition comprising: ~0.14 wt % SA3; ~0.14 wt % SA4; 0.34 wt % L2; and ~3 wt % acrylamide, corresponding to ~33.3% of the stoichiometric amount for complete hybridization. The elastic modulus was measured by affixing a thin, small loading surface fashioned from a microscopic slide cover slip to the top of the cylindrical sample. The surface was loaded with the tips of brass pins of various weights. Deflections were measured by focusing on the loading surface with an inverted microscope. Representative data of the stress-strain curve are illustrated in FIG. 8. The linear elastic modulus was determined from a curve fit to data such as that shown in FIG. 8. The linear elastic modulus is the elastic modules at zero strain. This was determined by extrapolating from the data points to zero strain. Since the data points depicted in FIG. 8 do not lie on a straight line a curve fit has to be performed and extended to zero strain.

The same gel composition was used to demonstrate the ability of the removal strand, R2, to facilitate the dissociation of SA3, SA4 and L2, and thereby convert the gel back to a fluid state. Micron-sized fluorescent beads were added to SA3 and SA4 before the addition of L2. The resulting gel after the addition of L2 was cut into several 0.2 mm$^2$ pieces. One such piece was immersed in a Well containing a 20 mL volume of a 1 mM solution of R2. Another piece of the gel, serving as a control was immersed in a Well containing 20 mL of TE buffer solution. The fluorescent beads served to increase the visibility of the gel, and allowed changes in size to be monitored as the gel dissolves and the beads become dispersed throughout the fluid volume. Photographs of both Wells were taken over regular intervals to monitor the rate of dissociation of the cross-linked gels. The dissociation of the cross-linked gel in the presence of the R2 strand occurred within 4 minutes as indicated by substantially complete dispersal of the fluorescent beads throughout the liquid contained in the first well. In comparison, the fluorescent beads in the second Well remained trapped in the gel for at least ~24 hours, at which time the experiment was terminated.

Figure 9:
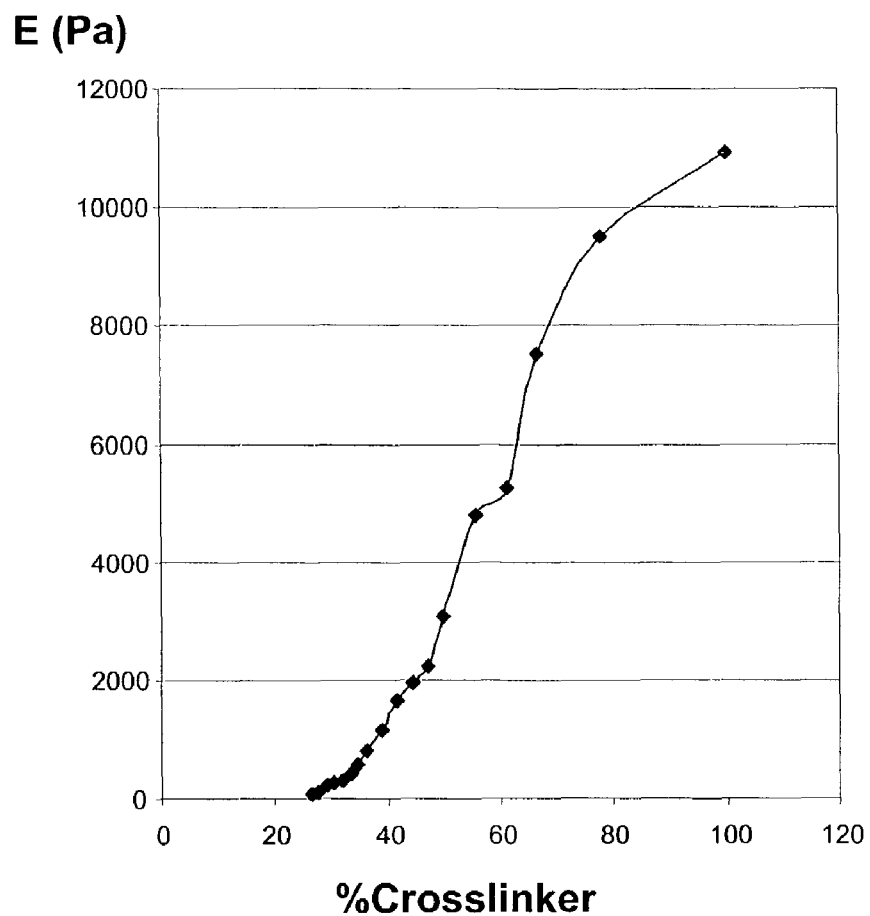
FIG. 9 illustrates the change in elastic modulus for representative compositions of the present invention having different amounts of a linking nucleic acid sequence.

The change in elastic modulus (E) of polyacrylamide gels, comprising 3 wt % acrylamide and with sidechains of SA1 and SA2, as a function of various amounts of the cross-linking L1 strand is shown in FIG. 9. A four order of magnitude increase in elastic modulus occurs as the amount of L1 increases from about 25 to about percent.

Although the present invention has been described in detail, those skilled in the art should understand that they can make various changes, substitutions and alterations herein without departing from the scope of the invention.

What is claimed is:

1. A modified or isolated composition, comprising:

a plurality of first polymers, each of said first polymers having first functional groups comprising a first nucleic acid sequence attached as side-chains thereto; and a plurality of second polymers, each of said second polymers having second functional groups comprising a second nucleic acid sequence attached as side-chains thereto, said first and said second functional groups forming a reversible cross-link between said first and said second polymers, wherein said cross-link comprises a plurality of hydrogen bonds between complementary base portions of said first and said second nucleic acid sequences, and wherein said composition is used as a prosthetic device capable of changing shape and elastic modulus as a function of an extent of said cross-links formed between said first and said second polymers and wherein said prosthetic device is selected from the group consisting of:

artificial spinal disk fluid;
artificial ligaments;
artificial bone;
artificial valves;
artificial skin; and
dental prostheses.

2. The composition as recited in claim 1, wherein said first and said second nucleic acid sequences are separately selected from the group consisting of:

deoxyribonucleic acid;
ribonucleic acid;
peptide nucleic acids; and
phosphorothioate analogues of DNA.

3. The composition as recited in claim 1, wherein at least ten bases in said first nucleic acid sequence form a sequence complementary to a base sequence in said second nucleic acid sequence.

4. The composition as recited in claim 1, wherein said first nucleic acid sequence and said second nucleic acid sequence each comprise between about 5 and about 100 nucleotide bases.

5. The composition as recited in claim 1, wherein said first functional groups comprises at least two first nucleic acid sequences having at least one difference in a base sequence between said first nucleic acid sequences, and wherein said second functional groups comprises at least two second nucleic acid sequences having at least one difference in a base sequence between said second nucleic acid sequences.

6. A modified or isolated composition, comprising:

a plurality of first polymers, each of said first polymers having first functional groups comprising a first nucleic acid sequence attached as side-chains thereto;

a plurality of second polymers, each of said second polymers having second functional groups comprising a second nucleic acid sequence attached as side-chains thereto, said first and said second functional groups capable of reversibly forming a reversible cross-link between said first and said second polymers wherein said cross-link comprises a plurality of hydrogen bonds between complementary base portions of said first and said second nucleic acid sequences; and a third nucleic acid sequence, wherein at least one of said first nucleic acid sequence or said second nucleic acid sequence further comprise a nucleic acid sequence that is sufficiently complementary to said third nucleic acid sequence that said third nucleic acid sequence facilitates a dissociation of said cross-link.

7. The composition as recited in claim 1, further including a third nucleic acid sequence capable of attaching to said first and said second nucleic acid sequences to facilitate formation of said cross-link.

8. A modified or isolated composition, comprising:
a plurality of first polymers, each of said first polymers having first functional groups comprising a first nucleic acid sequence attached as side-chains thereto;
a plurality of second polymers, each of said second polymers having second functional groups comprising a second nucleic acid sequence attached as side-chains thereto, said first and said second functional groups forming a reversible cross-link between said first and said second polymers, wherein said cross-link comprises a plurality of hydrogen bonds between complementary base portions of said first and said second nucleic acid sequences;
a third nucleic acid sequence capable of attaching to said first and said second nucleic acid sequences to facilitate formation of said cross-link; and
a fourth nucleic acid sequence, wherein said third nucleic acid sequence further comprises a nucleic acid sequence that is sufficiently complementary to said fourth nucleic acid sequence that said fourth nucleic acid sequence facilitates a dissociation of said cross-link.

\* \* \* \* \*